United States Patent [19]

Yano et al.

[11] 4,269,682

[45] May 26, 1981

[54] REFERENCE ELECTRODE OF INSULATED GATE FIELD EFFECT TRANSISTOR

[75] Inventors: Makoto Yano; Kiyoo Shimada; Kyoichiro Shibatani; Tsutomu Makimoto, all of Kurashiki, Japan

[73] Assignees: Kuraray Co., Ltd.; Tadayuki Matsuo, both of Sendai, Japan

[21] Appl. No.: 968,418

[22] Filed: Dec. 11, 1978

[30] Foreign Application Priority Data

Dec. 12, 1977 [JP] Japan ............................ 52/150093

[51] Int. Cl.³ .............................................. G01N 27/46
[52] U.S. Cl. ............................ 204/195 M; 204/195 F
[58] Field of Search ..................... 204/195 F, 195 M

[56] References Cited

U.S. PATENT DOCUMENTS

| 3,591,482 | 7/1971 | Neff et al. ................ 204/195 F |
| 3,831,432 | 8/1974 | Cox ........................... 204/195 R |
| 3,856,649 | 12/1974 | Genshaw et al. .......... 204/195 F |
| 4,020,830 | 5/1977 | Johnson et al. ............ 204/195 M |
| 4,133,735 | 1/1979 | Afromowitz et al. ...... 204/195 M |

OTHER PUBLICATIONS

Matsuo et al., "IEEE, Trans. on BME", vol. BMZ-21, No. 6, pp. 485-487, (1974).
Japanese Published Unexamined Patent Application No. 52-26292, (Feb. 1977).
Comte et al., "Reference ISFET For Compensation", Proc. of the 30th Annual Conf. on Engr. in Medicine and Biology, p. 298, Nov. 5-9, 1977.
Matsuo et al., "Characteristics of Parylene Gate ISFET", Extended Abstracts of Corrosion, Division of the Electro-Chemical Society, Inc. Abstract No. 83, Spring Meeting, Seattle, Washington, May 21-22, 1978.

Primary Examiner—T. Tung
Attorney, Agent, or Firm—Oblon, Fisher, Spivak, McClelland & Maier

[57] ABSTRACT

A reference electrode of an insulated gate field effect transistor having the surface of the gate region thereof coated with a hydrophobic organic polymer membrane. Since this reference electrode is much smaller in size than conventional reference electrodes, an integrated measurement system can easily be constructed by using this reference electrode. This measurement system is especially effective for measuring various ions in the living body.

18 Claims, 7 Drawing Figures

REFERENCE ELECTRODE OF INSULATED GATE FIELD EFFECT TRANSISTOR

BACKGROUND OF THE INVENTION

1. Field of the Invention

This invention relates to a reference electrode of an insulated gate field effective transistor (hereinafter referred to as "FET") and also to a system for selective detection and measurement of chemical properties of substances which this reference electrode comprises. The term "chemical properties" is used in this invention to include the activity and concentration of ions, the presence and concentration of enzymes, substrates, antibodies, antigens, hormones and reducible gases and the presence, concentration and activity of various chemical substances and biochemical substances. More particularly, the invention relates to a system for selective detection and measurement of the activity and concentration of ions.

2. Description of the Prior Art

Glass electrodes have heretofore been used for selective measurement of quantities of chemical substances in samples. Electrodes of this type are valuable for selective determination of activities of chemical substances, especially various ions in the living body, in the medical and physiological fields. In these conventional electrodes, however, since the resistance of the glass film is about 10 MΩ, a high input resistance amplifier should be used. Further, the glass film is thin and is poor in the mechanical strength. Moreover, when the quantity of a specific chemical substance existing in a very small volume location is to be measured, since the contact area of the glass electrode with the substance should be small, the resistance of the glass film is especially increased. Accordingly, it is difficult to insulate portions other than the top end portion in the electrode. Therefore, when an electrode of this type is employed, it is technically difficult to measure the quantity of a specific chemical substance in a small volume location.

Recently, a novel small size sensor, in which the foregoing defects of glass electrodes are eliminated, was proposed by K. D. Wise et al. in IEEE, Trans. on BME, Vol. BME-21, No. 6, pp. 485–487, 1974. According to this proposal, a gate insulated FET is used, in which silicon nitride, excellent in water resistance, is further coated on the surface of an insulated gate layer composed of silicon dioxide, and the precision of measurement in aqueous solutions is improved by adoption of this structure. Such an FET can be used as a sensor sensitive to the hydrogen ion. In the above report, K. D. Wise et al. suggested that an FET having the above structure would possibly be a sensor capable of selectively detecting various chemical substances. Further, the structure of an FET which can selectively detect and measure various chemical properties is disclosed in U.S. Pat. No. 4,020,830. The disclosed sensor has an insulated gate layer composed of silicon dioxide or silicon nitride and a layer having a chemical selectivity, such as used in a glass electrode, which is coated on the surface of the insulated gate layer. By utilizing this sensor, such ions as sodium ions and potassium ions can be measured.

Still further, Japanese patent application Laid-Open Specification No. 26292/77 discloses an FET sensor comprising an insulated gate layer composed of silicon dioxide, silicon nitride and a top layer selectively sensitive to specific chemical substances, which is coated on the insulated gate layer.

In the above-mentioned FET sensor, the size can be decreased and the defect inherently involved in a glass electrode, namely a high electrode resistance, be eliminated. Therefore, this sensor can be advantageously used as a miniature electrode, especially in the medical and biological fields. When such sensor is used, however, it is indispensable to employ a reference electrode providing a certain potential difference irrespectively of the ion concentration in a liquid to be tested.

Electrodes dipped in an internal reference solution, such as a calomel electrode, a silver chloride electrode and a mercuric oxide electrode, have heretofore been used as reference electrodes, and electrodes of thisin a liquid to be tested.

Electrodes dipped in an internal reference solution, such as a calomel electrode, a silver chloride electrode and a mercuric oxide electrode, have heretofore been used as reference electrodes, and electrodes of this type are also disclosed in U.S. Pat. No. 4,020,830. In such a reference electrode, an internal reference liquid should be contacted with a solution to be tested through a liquid junction. These reference electrodes are divided into three types, namely the pinhole type, the sleeve type and the fiber type according to the structure of the liquid junction. In each type, if the size of the liquid junction is diminished in order to prevent the internal reference solution from flowing out, measurement values become unstable, because of increase of the resistance. Accordingly, it is necessary to maintain a certain size in the liquid junction, and hence, flow-out of the internal reference solution from the liquid junction cannot be avoided. Therefore, if flow-out of the internal reference solution is taken into account, it is not permissible to reduce the quantity of the internal reference solution below a certain level and hence, diminution of the size of the reference electrode is limited. Therefore, even if a very small size FET sensor is used, since the size of a reference electrode to be used in combination is large, a minute substance cannot be measured and the measurement is impossible in a small vessel. For this reason, it has been desired in the art to develop a small size reference electrode capable of allowing an FET to exert characteristics thereof sufficiently.

Recently, several reference electrodes meeting this objective have been proposed. For example, in the 30th Annual Conference on Engineering in Medicine and Biology, J. Janata proposed a reference electrode in which an FET sensor is dipped in an internal reference solution instead of a silver chloride electrode customarily used for the conventional reference electrode and is contacted with a liquid to be tested through a liquid junction. In this proposal, since an FET is used instead of the conventional reference electrode, the size can be decreased to some extent, but since an internal reference solution is employed, decrease of the size is inevitably limited. Further, it is very difficult to manufacture a minute electrode having such structure. Separately, Japanese patent application Laid-Open Specification No. 26292/77 discloses that an FET sensitive to a substance of a constant concentration in a liquid to be tested is used as a reference electrode. As one example of such means, there is proposed a reference electrode comprising silver-silver chloride coated on the surface of a gate region of FET. This electrode acts as a sensor selectively detecting the concentration of chlorine ions. Accordingly, this electrode can be used as a reference electrode in the tissue of a living body where the chloride ion concentration is constant. This electrode, however, is defective in that since the potential is changed according to the chlorine ion concentration, it can be applied to limited uses alone.

SUMMARY OF THE INVENTION

It is therefore a primary object of this invention to provide a reference electrode of an insulated gate field effect transistor, which is not sensitive to chemical properties but is selectively sensitive to the potential of a liquid to be tested.

Another object of this invention is to provide a reference electrode having a much smaller size.

Still another object of this invention is to provide a reference electrode which can be used in combination with a unit for measurement of chemical properties comprising an insulated gate field effect transistor, which is sensitive to chemical properties in liquids to be tested.

A further object of this invention is to provide a system for measurement of chemical properties, which comprises a reference electrode of an insulated gate field effect transistor.

A still further object of this invention is to provide a system for measurement of chemical properties, which has a much diminished size and is effective for detecting and measuring various ion concentrations in a living body.

A still further object of this invention is to provide an integrated composite measurement system in which a unit for measurement of chemical properties and a reference electrode are integrally built.

In accordance with this invention, these objects can be attained by a reference electrode comprising an insulated gate field effect transistor having the surface of a gate region thereof coated with a hydrophobic organic polymeric membrane.

DETAILED DESCRIPTION OF THE PREFERRED EMBODIMENTS

Figure 1A:
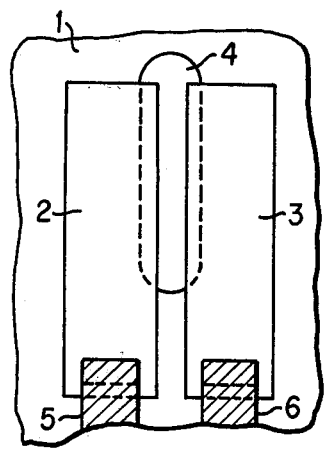
FIGS. 1-A and 1-B illustrate one embodiment of the reference electrode of this invention.

The reference electrode of this invention can be constructed by using a known insulated gate FET. Such known insulated gate FET is disclosed, for example, in the paper by K. D. Weise et al, U.S. Pat. No. 4,020,830 and Japanese patent application Laid-Open Specification No. 26292/77 and herewith incorporated by reference. The gate-insulating layer of the FET is ordinarily composed of silicon dioxide or silicon nitride. A gate-insulating layer having a two-layer structure comprising a silicon dioxide layer and a silicon nitride layer formed thereon is especially preferred.

We found that a reference electrode can be manufactured by coating a gate-insulating layer with a hydrophobic organic polymeric membrane. In the case where the surface of an insulated gate is composed of an oxide or nitride, an interfacial potential is considered to be generated by hydrogen ions or the like according to the dissociation equilibrium of hydroxyl groups on the surface. In contrast, if the surface is coated with a hydrophobic organic polymer membrane free of an ionic dissociative group, since a liquid to be tested is not allowed to contact the gate surface, no interfacial potential is generated, and therefore, such electrode can be effectively used as a reference electrode.

As will be apparent from the foregoing illustration, in this invention, an organic polymer membrane to be formed on the gate surface should be so water-impermeable that the gate surface is prevented from falling in contact with a liquid to be tested. Hydrophobic membranes are ordinarily water-impermeable. In this invention, by the "hydrophobic membrane" is meant a membrane in which the degree of water content is lower than 0.5% by weight. In this invention, the degree of water content is one determined with respect to a membrane formed with the same conditions as the membrane to be coated on a gate region, according to the method of ASTM D570-63. As is illustrated in Examples given hereinafter, an electrode provided with such membrane is not sensitive to ions in a liquid to be tested.

U.S. Pat. No. 4,020,830 mentioned above discloses a sensor comprising an insulated gate FET coated with a hydrophobic membrane. However, the disclosed hydrophobic membrane indispensably contains a liquid capable of selectively adsorbing specific substances and rendering the gate surface sensitive to chemical properties. Accordingly, an electrode coated with such membrane can be used as a sensor but cannot be used as a reference electrode. The hydrophobic organic polymer membrane of this invention does not contain such ligand at all and therefore, it is not sensitive to chemical properties in a liquid to be tested but is only sensitive to the potential of a liquid to be tested.

As the polymer that constitutes the hydrophobic organic polymer in this invention, there can be used any of polymers of carbon-containing compounds having a film-forming molecular weight corresponding to a degree of polymerization of at least 100, and the kind of the carbon-containing polymer and the upper limit of the degree of polymerization are not critical. Cross-linkages may be introduced into the polymeric membrane coating.

In this invention, the kind of the hydrophobic organic polymer is not critical as pointed out above, but the use of polymers formed by polymerizing a vinyl monomer or monomers selected from the group consisting of monoolefins, halogenoethylenes, conjugated dienes and halogenated conjugated dienes is preferred. As the monoolefin, there can be mentioned those having 2 to 5 carbon atoms, such as ethylene, propylene, butene and isobutene, and among them, ethylene is especially preferred.

As the halogenoethylene, there are preferably employed compounds represented by the following general formula:

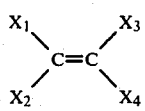

wherein $X_1$, $X_2$, $X_3$ and $X_4$ each stand for an atom selected from the group consisting of hydrogen, chlorine and fluorine with the proviso that the case where all of $X_1$, $X_2$, $X_3$ and $X_4$ stand for a hydrogen atom is excluded. For example, there can be mentioned vinyl chloride, vinylindene chloride, vinyl fluoride, trifluoroethylene, tetrafluoroethylene and tetrachloroethylene.

As the conjugated diene or halogenated conjugated diene, there are preferably employed compounds represented by the following general formula:

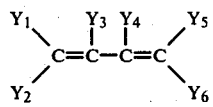

wherein $Y_1$ to $Y_6$ stand for a member selected from the group consisting of a hydrogen atom, a chlorine atom, a fluorine atom and alkyl groups having 1 to 3 carbon atoms. For example, there can be mentioned butadiene, chloroprene, isoprene and hexachlorobutadiene. Among these compounds, butadiene and hexachlorobutadiene are especially preferred.

Either homopolymers of the foregoing monomers or copolymers obtained by polymerizing at least two members selected from the foregoing monomers can be used in this invention. From the viewpoint of the stability of the potential, it is preferred to select, among the above-mentioned polymers, a homopolymer of trifluoroethylene, a homopolymer of tetrafluoroethylene, a trifluoroethylenetetrafluoroethylene copolymer, a homopolymer of vinyl chloride, a homopolymer of vinylidene chloride and a vinyl chloride-vinylidene chloride copolymer. The reason is that such halogen-containing polymer can easily be formed into a thin membrane and the resulting membrane has a high polarity.

As another type of the hydrophobic organic polymer that can be used in this invention, there can be mentioned polysiloxanes represented by the following general formula:

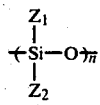

wherein $Z_1$ and $Z_2$ stand for an alkyl or aryl group having 1 to B 10 carbon atoms in which one or more of the carbon atoms have a substituent such as a chlorine or bromine atom or a cyano group, and n is a number of at least 100. Since these polysiloxanes have a very high hydrophobic characteristic, they are preferably employed. As such polysiloxane, there can be mentioned, for example, polydimethylsiloxane, polyphenylsiloxane, polydecylsiloxane, polytrimethylsiloxane, polychlorophenylsiloxane, polymethylphenylsiloxane and polycyanoethylsiloxane. Among these siloxanes, there are especially preferably employed polydimethylsiloxane and polydiphenylsiloxane. In the above general formula, $Z_1$ and $Z_2$ may be different from each other. Further, not only homopolymers but also copolymers, such as copolymers including dimethylsiloxane units and diphenylsiloxane units and block copolymers thereof, can be used. Further, these polysiloxanes may be used in the form of block copolymers with other hydrophobic polymers, such as polycarbonate.

In order to improve the chemical resistance and mechanical strength in the resulting membrane, it is preferred that at the step of applying such polysiloxane to the gate surface, a cross-linking agent such as an alkoxysilane, a hydroxysilane, an oxime silane or an acetoxysilane is incorporated into the polysiloxane and the cross-linking treatment is carried out after the coating step.

In addition, monomers capable of forming hydrophobic polymers, such as styrene, divinylbenzene, acrylonitrile, acrolein, vinyl acetate, methyl methacrylate, butyl acrylate, vinylidene cyanide, chlorostyrene and chloromethylstyrene may be used as the starting compound for formation of a hydrophobic polymeric membrane in this invention.

In this invention, polymers derived from the above-mentioned various monomers can be used as membrane-forming materials, but polymers composed of monomers having dissociative groups such as carboxyl, amino and hydroxyl groups cannot be used because they are hydrophilic and have a degree of water content exceeding 0.5%.

It is indispensable that the polymer membrane that is used in this invention should not have pinholes, which give bad influences on the electrode stability. It is preferred that the membrane be as thin as possible, so far as pinholes are not present. When the thickness is large, an induced current having an influence on measured values is generated. So, the stability to the output change is gradually degraded with the increase of the thickness. The thickness of the membrane is ordinarily 500 Å to 1$\mu$ and preferably 1000 to 3000 Å.

In this invention, it is preferred that the surface of the gate region be treated with a silane coupling agent prior to formation of a polymeric membrane. If a polymeric membrane is formed without giving this silanation treatment, on dipping the coated FET into an aqueous solution for a long time, water will intrude between the gate surface of FET and the polymeric membrane, and the FET becomes ion sensitive. As the silane coupling agent, there can be mentioned, for example, compunds represented by the formula $CH_2=CHSi(OR)_3$ or $CH_2=C(CH_3)COOCH_2CH_2CH_2Si(OR)_3$ in which R stands for an alkyl group having 1 to 3 carbon atoms. The silanation treatment may be carried out according to a conventional method.

As the method for forming a polymeric membrane on the surface of the gate region, there can be mentioned, for example, (i) a method in which a hydrophobic organic polymer is dissolved in an appropriate solvent, the resulting solution is coated on the surface of the gate region and the solvent is then evaporated, and (ii) a method in which a monomer capable of forming a hydrophobic organic polymer or a monomer solution containing a partially polymerized product is applied to the surface of the gate region and polymerization is caused to proceed on the surface of the gate region to form a polymeric membrane.

In the method (i), any of polymers obtained by polymerizing the above-mentioned monomer according to known polymerization methods can be used as the polymer. The polymerization conditions are not particularly critical. In order to improve the film-forming property, the dielectric property and the electric conductivity of the polymer, additives such as non-ionic plasticizers and carbon may be incorporated into the membrane-constituting polymer. Especially when polyvinyl chloride is used, by incorporating 100 to 400 parts by weight of a plasticizer such as dioctyl phthalate, dioctyl adipate or tricresyl phosphate into 100 parts by weight of polyvinyl chloride, the film-forming property can be remarkably improved, and in this case, a stable thin film can be formed on the surface of the gate region. It is preferred that the coating operation of the polymer solution on the surface of the gate region be conducted several times and the solvent be slowly evaporated after the coating operation.

In the above-mentioned method (ii), it is preferred that a polymeric membrane be formed by plasma polymerization, ultraviolet polymerization or radiation polymerization. Such polymerization can be accomplished according to conventional polymerization techniques, and such conditions as the vapor pressure of the monomers, the polymerization temperature, the polymerization time and the dose of plasma, ultraviolet rays or actinic rays can be appropriately chosen.

In this invention, it is indispensable that a polymeric membrane should be formed at least on the gate region. It is preferred that the entire surface of the FET be coated with the polymeric membrane, because the coating process is simpler and there is no risk of insulation breakdown.

In measuring chemical properties by using the reference electrode of this invention, it is necessary to use a unit for measuring chemical properties and a pseudo reference electrode in combination.

Since the reference electrode of this invention is an insulated gate electrode, it is necessary to use independently a pseudo reference electrode to apply bias, and by the use of the pseudo reference electrode, the potential of an electrolyte solution is fixed and the difference of the output potential between the measuring unit and the reference electrode is detected based on the fixed potential of the electrolyte solution. For this detection, there is used a differential amplifier. In this case, the potential $E_O$ of the pseudo reference electrode is the in-phase input voltage of the differential amplifier and has no influences on the output voltage $V_O$ of the differential amplifier. In other words, the following relation is established:

Output voltage α [ion sensor output $(E_1 - E_0)$]
  − [reference electrode output
  $(E_R - E_0)] = E_1 - E_R$ Accordingly, any conductor can be used for the pseudo reference electrode. For example, an appropriate metal such as gold, silver or platinum or graphite may be used. The shape of the pseudo reference electrode is not particularly critical, so far as it is constructed so that the electrode is allowed to fall in contact with a liquid to be tested. Although the potential should be stable in the reference electrode, in the pseudo reference electrode the potential need not be kept stable. Therefore, the pseudo reference electrode can easily be manufactured. For example, if a support of the FET sensor described hereinafter is formed of a metal, this support acts as a pseudo reference electrode.

The unit for measuring chemical properties, which is used in combination with the reference electrode of this invention, comprises an insulated gate FET sensitive to chemical properties in a liquid to be tested. An FET as disclosed in the above-mentioned prior art references can be used in this invention. The above-mentioned insulated gate FET having a gate-insulating layer of a double layer structure comprising a silicon dioxide layer and a silicon nitride layer is a preferred pH sensor, and an insulated gate FET sensor having a membrane selectively sensitive to a specific chemical substance, that is used for a glass electrode or the like, on the surface of a gate region of an ordinary FET, can be used for measuring various chemical properties described hereinbefore especially the concentration and activity of ions in electrolytes, according to the characteristics of the membrane.

As an example of the membrane having a selective sensitivity, there can be mentioned an inorganic membrane of an alkali metal silicate glass or the like or an organic membrane containing a ligand to a specific substance. As the former silicate glass, there can be mentioned, for example, a glass of $SiO_2/CaO/Na_2O$ (72.2/6.4/21.4 molar ratio) which can be used for detection and measurement of pH and $pNa^+$. As the ligand to a specific substance, that is included in the latter membrane, there can be mentioned, for example, antibiotics such as Valinomycin and Nonactin and cyclic ligands such as crown ether and cryptant. As the membrane-constituting material, there can be mentioned, for example, polyvinyl chloride, celluloses, polyurethane and polystyrene, which may contain a plasticizer. Such ligand-containing membrane is effective for detecting and measuring sodium, potassium, calcium, barium and the like. As another example of the membrane selectively sensitive to specific chemical substances, there can be mentioned an antibody membrane, a hem membrane and a silver halide membrane. Antigens oxygen gas and halogens can be detected and measured by these membranes, respectively. Further, various membranes disclosed in U.S. Pat. No. 4,020,830 can be used in this invention. Still further, in this invention there can be used a multi-sensor having a selective sensitivity to different chemical substances. The multi-sensor may be plural FET's which are formed on a single silicon chip.

Figure 1B:
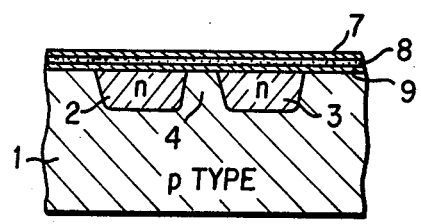

FIGS. 1-A and 1-B illustrate the gate region of one embodiment of the reference electrode of this invention, which comprises an insulated gate FET having the gate region coated with a hydrophobic organic membrane. In the drawing, reference numeral 1 represents a p-type silicon substrate, and reference numerals 2 and 3 represent n-type diffusion layers of source and drain, respectively. Reference numeral 4 represents a channel, and reference numerals 5 and 6 represent a terminal of source and drain, respectively. Reference numerals 7 and 8 represent a silicon nitride layer and a silicon oxide layer, respectively. These layers 7 and 8 have a thickness of 1000 Å and constitute a gate-insulating layer. A polyvinyl chloride membrane 9 having a thickness of 1000 Å is formed on the gate-insulating layer.

Figure 3:
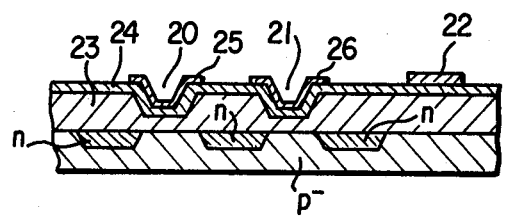
FIG. 3 is a view showing the section taken along the line A—A in the pH measuring system shown in FIG. 2.

An embodiment of the measurement system of this invention, comprising a chemical property measuring unit, a pseudo reference electrode and a reference electrode, will now be described by reference to FIGS. 2 to 4.

Figure 2:
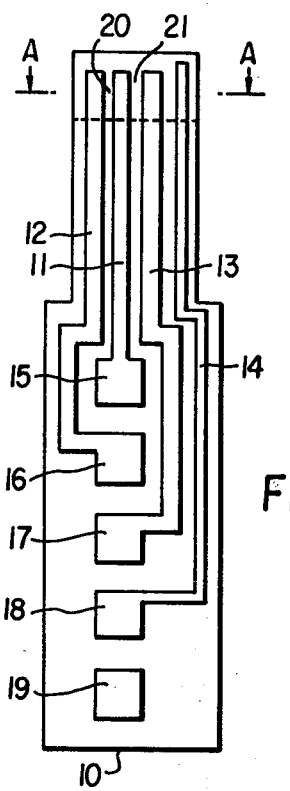
FIG. 2 is a plan view showing one embodiment of a pH measuring system comprising a pH sensor, a reference electrode and a pseudo reference electrode, which are formed on one silicon wafer.

FIG. 2 is a plan view illustrating an integrated measurement system comprising and FET sensor, a pseudo reference electrode and a reference electrode, each of which is formed on one silicon wafer 10. Reference numerals 11, 12 and 13 represent n-type silicon grooves formed on p-type silicon. More specifically, reference numeral 11 represents a common drain, reference numeral 12 represents a source of the reference electrode and reference numeral 13 represents a source of the sensor. Reference numeral 14 represents a pseudo reference electrode necessary for maintaining the potential of a liquid to be tested at a constant level, which is formed by vacuum deposition of gold. Reference numerals 15, 16, 17, 18 and 19 represent electrode portions of the common drain, reference electrode source, sensor source, pseudo reference electrode and substrate, respectively. Reference numerals 20 and 21 represent gate regions of the reference electrode and sensor, respectively. FIG. 3 is a view showing the section taken along the line A—A in FIG. 2, in which reference numerals 20, 21 and 22 represent the gate region of the reference electrode, the gate region of the sensor and the pseudo reference electrode, respectively. In the gate regions of the sensor and reference electrode, an ion-sensitive membrane 26 and a hydrophobic organic membrane 25 are coated, respectively, on a two-layer structure of silicon dioxide 23 and silicon nitride 24. If a two-layer structure of silicon dioxide 23 and silicon nitride 24 is formed on the gate region of the sensor, the system can be used as a pH sensor. Such sensor can be manufactured by a customary IC manufacturing technique according to a known method disclosed in, for example, Japanese patent application Laid-Open Specification No. 96890/78 herewith incorporated by reference.

This integrated ion sensor system can be manufactured according to the following procedures.

At first, two electrodes 20 and 21 are formed on one silicon wafer. The surface of these regions is formed of a silicon nitride layer, and a gold electrode 14 is formed as a pseudo reference electrode by vacuum deposition of gold. Since the stability of the electrode potential and the like are of no particular significance in this pseudo reference electrode, an appropriate material capable of facilitating the integration operation can be used for this electrode. When the pseudo reference electrode is formed of gold, an undercoating of chromium having a thickness of about 1000 Å is formed by vacuum deposition and a gold layer having a thickness of about 1000 Å is formed thereon by vacuum deposition. When chromium is thus used, the adhesion of the gold electrode to the substrate can be improved.

Then, polyvinyl chloride is coated in a thickness of about 1000 Å on the gold electrode. The polyvinyl chloride membrane is left only in the area of the reference electrode 20 and in another area, the polyvinyl chloride membrane is removed. More specifically, aluminum is vacuum-deposited in a thickness of about 1000 Å in the area of the reference electrode, and by using the so formed aluminum layer as a mask, the polyvinyl chloride membrane is removed from the area of the pH sensor 10 and the area of the gold electrode 14 by etching in oxygen plasma generated by a high frequency wave of 13 MHz (the frequency is not particularly critical) under an oxygen pressure of about 0.5 torr. Then, the aluminum layer used as the mask for etching of the polyvinyl chloride layer is removed by a phosphoric acid type etching solution. Thus, an integrated measurement system as shown in FIG. 2 is manufactured.

This measurement system comprises a sensor, a reference electrode and a pseudo reference electrode, each of which is formed on one silicon wafer. When these members are thus formed on one silicon wafer, a measurement system having a very small size can be prepared very easily. Therefore, this system can be said to be a most preferred embodiment of the measurement system of this invention. Of course, there may be adopted a method in which the foregoing three elements are separately prepared, or a method in which two of the foregoing three elements are formed on one silicon wafer.

Figure 4:
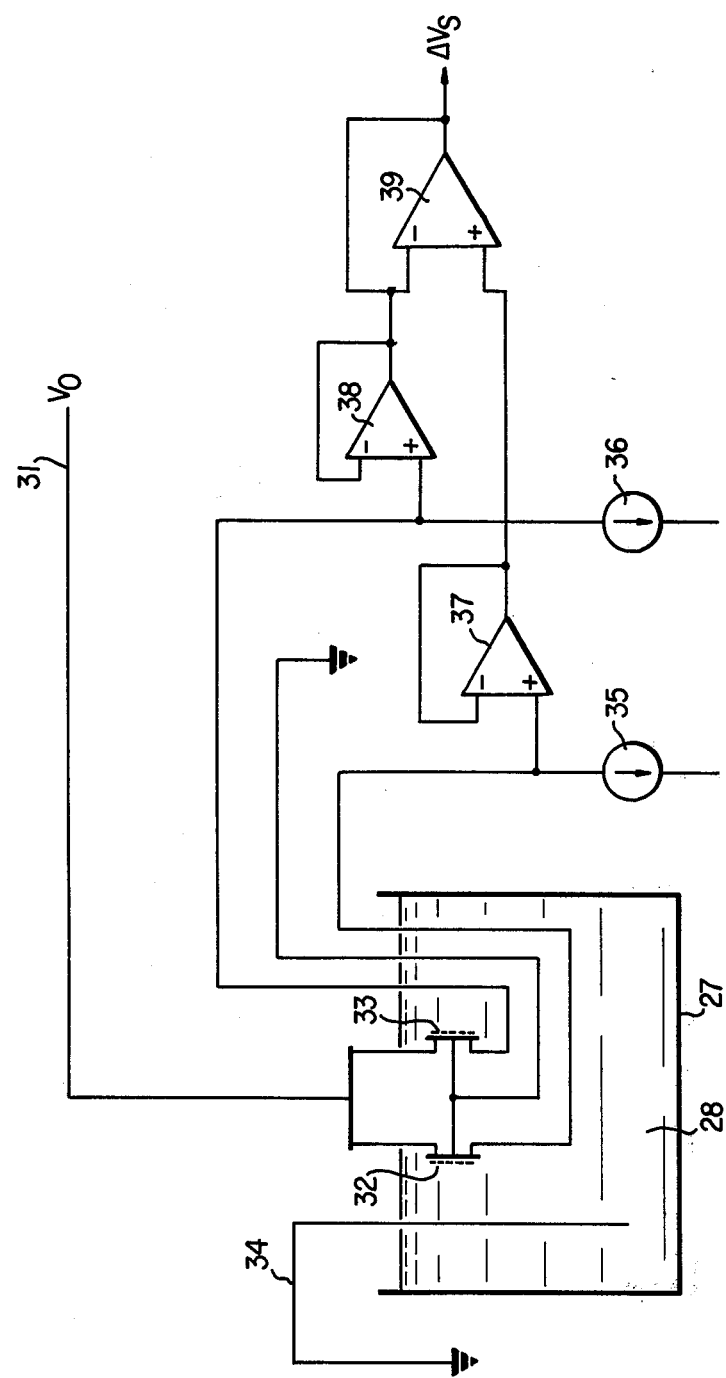
FIG. 4 is a diagram illustrating one embodiment of an electric circuit including the pH measuring system shown in FIG. 2.

FIG. 4 is a view illustrating diagrammatically an instance of the measuring circuit including the system illustrated in FIG. 2. Referring to FIG. 4, the measurement system is put in a liquid 28 to be tested, which is contained in a vessel 27. A constant voltage power source 31 is a common power source for a sensor 33 and a reference electrode 32, which is used for actuating the reference electrode and sensor in the saturation region. Reference numerals 35 and 36 represent constant current devices for maintaining constant electric currents for FET 32 and FET 33. Reference numeral 34 represents a pseudo reference electrode for maintaining the potential of the liquid to be tested at a constant level. The source voltages (outputs) of the sensor and reference electrode are amplified by impedance conversion circuits 37 and 38, respectively, and the output difference is detected by a subtracting circuit 39. This output difference is an output $\Delta Vs$ corresponding to the measured ion concentration, etc.

By using the reference electrode of this invention, the size of the measurement system can be decreased and especially when this reference electrode and a chemical property measuring unit including an insulated gate FET are formed on one silicon wafer, there can be obtained an integrated measurement system having a much diminished size. If such measurement system is used, the activity of specific ions can be measured without the effect of electric potential (for example, action/-potential of a living body) in an electrolyte solution. This feature provides characteristic advantages when the measurement system is used as an ion sensor for a living body. In the case of a conventional ion sensor not using the reference electrode of this invention, changes of the electric potential in an electrolyte solution would generate noises for the output of the ion sensor.

Embodiments of this invention will now be described in detail by reference to the following examples that by no means limit the scope of the invention.

EXAMPLE 1

Figure 5:
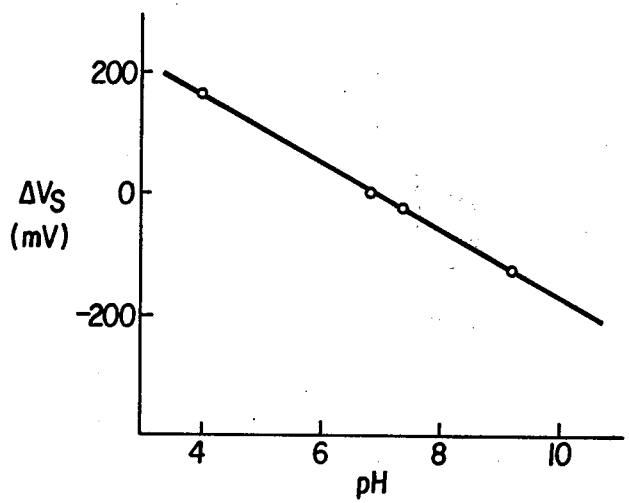
FIG. 5 is a diagram illustrating the relation of the output difference in source voltages of the pH sensor and reference electrode to the pH value in the circuit shown in FIG. 4.

A solution of 5 mg of polyvinyl chloride (Geon 400X150P manufactured by Japanese Geon Co., Ltd.) and 5 mg of dioctyl phthalate in 150 ml of tetrahydrofuran was coated on the gate region of an FET having a two-layer structure of silicon dioxide and silicon nitride (disclosed in Japanese patent application Laid-Open Specification No. 96890/78 and herewith incorporated by reference) and the coating was dried to form the reference electrode. A circuit as shown in FIG. 4 was constructed by using the so formed reference electrode in combination with the above FET which was not subjected to the above coating treatment as a pH sensor. The relation between the pH and the output difference $\Delta Vs$ in the source voltages of the FET sensor and the reference electrode, which was observed in the so constructed circuit, is shown in FIG. 5. In this experiment, a silver wire was used as the pseudo reference electrode and the measurement was carried out at a drain voltage of 1.5 V and a drain current of 30 $\mu A$. A pH buffer solution described in JIS 28802-1954 incorporated by reference was used as the buffer solution and human blood was used as a liquid to be tested.

From the results shown in FIG. 5, it can readily be understood that a good linear relation is established between the pH and $\Delta V$s irrespectively of the kind and concentration of ions. Thus, it has been confirmed that an FET coated with a polyvinyl chloride membrane can be satisfactorily used as a reference electrode.

EXAMPLE 2

A membrane of a polymeric substance indicated in Table 1 is formed on the gate region of the same FET as used in Example 1 by the following coated procedures.

At first, a polymer solution having a concentration indicated in Table 1 was prepared and the gate region of FET was dipped in the solution. The dipped FET was sufficiently shaken to remove the excessive solution, and the solvent was removed by drying.

In order to check whether the so formed electrode could be used as a reference electrode, the pH sensitivity of the electrode was determined according to the following method, and when the pH sensitivity was lower than 5 mV/pH, it was judged that the electrode could be used as a reference electrode.

PH DETERMINATION METHOD

Figure 6:
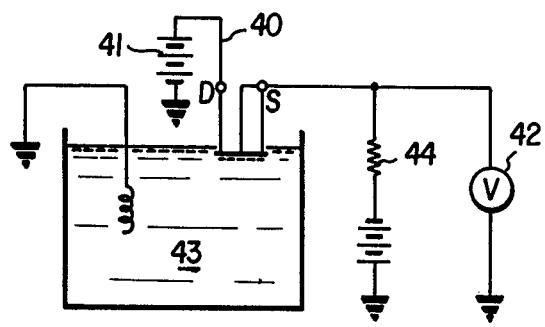
FIG. 6 is a diagram illustrating a circuit for measuring the ion activity in an electrolyte solution.

The formed electrode was used as a pH sensor and a calomel electrode was used as a reference electrode. The pH buffer solution described in Example 1 was used as a liquid to be tested. A measurement circuit used is shown in FIG. 6, in which reference numeral 40 represents the pH sensor, reference numeral 41 represents the reference electrode for maintaining the potential of the liquid to be tested at a certain level, and reference numeral 42 represents a voltage meter indicating the surface potential of the gate-insulating layer. On the pH sensor side, there was employed a source follower circuit of a low output resistance including a resistance 44 connected to the source, and the output of this circuit was displayed on the voltage meter. The source voltage was measured under conditions of a drain current of 30 $\mu$A and a drain voltage of 5 V.

The results thus obtained are shown in Table 1. From these results, the following can be seen.

When the electrode is coated with a hydrophobic polymer having a degree of water content lower than 0.5% as in runs nos. 1 and 2, the sensitivity to the pH is apparently low. Accordingly, it is seen that an electrode coated with a hydrophobic membrane can be used as a reference electrode.

In contrast, when an electrode is coated with a hydrophilic membrane having a high degree of water content, the sensitivity to the pH is very high and this electrode cannot be used as a reference electrode.

Incidentally, when the polymer solutions of runs nos. 1 and 2 were separately coated on glass sheets in the same manner, the thickness of the formed membrane was 2000 Å in case of the polymer solution of run No. 1 and 3000 Å in case of the polymer solution of run no. 2.

TABLE 1

| Run No. | Polymer (degree of water content, %) | Polymer Solution solvent | Concentration (% by weight) | Source Voltage pH 4 | pH 7 | pH 9 |
|---|---|---|---|---|---|---|
| 1 | polydimethylsiloxane[a] (0.0) | dimethyl ether | 0.5 | 1.194 | −1.195 | −1.196 |
| 2 | vinyl chloride-vinylidene chloride copolymer[b] (0.3) | tetrahydrofuran | 2 | 1.442 | 1.446 | 1.433 |
| 3 | polyvinyl alcohol[c] (water-soluble) | water | 0.5 | 0.682 | 0.515 | 0.396 |
| 4 | polyhydroxyethyl methacrylate[d] (60) | 95% ethanol | 2 | 1.156 | 1.005 | 0.897 |
| 5 | hydroxy methacrylate-methyl methacrylate copolymer[e] (5) | acetone | 1 | 0.326 | 0.188 | 0.090 |
| 6 | untreated | — | — | 1.165 | 1.007 | 0.884 |

Note
[a]Silicone KE44 manufactured by Shinetsu Kagaku Kogyo Co., Ltd.
[b]vinyl chloride/vinylidene chloride copolymer (5/95 molar ratio) obtained by solution polymerization using cyclohexanone as the solvent and azobisisobutyronitrile as the catalyst
[c]Kuraray Poval 117 manufactured by Kuraray Co., Ltd.
[d]polymer obtained by solution polymerization of hydroxyethyl methacrylate by using pure ethanol as the solvent and isopropyl percarbonate as the catalyst
[e]hydroxyethyl methacrylate/methyl methacrylate copolymer (20/80 molar ratio) obtained by solution polymerization using ethanol as the solvent and isopropyl percarbonate as the catalyst

EXAMPLE 3

The surface of the gate region of the same FET as used in Example 1 was treated with a 5% aqueous solution of vinyl-$\beta$-methoxyethoxysilane and a hydrophobic membrane was prepared on the surface of the gate region by ultraviolet polymerization according to the following procedures.

The surface-treated FET was placed in a quartz tube and the interior of the tube was evacuated to $10^{-3}$ mm Hg using a vacuum line. Then, vinylidene chloride of 80 mm Hg and vinyl chloride of 20 mm Hg were introduced into the interior of the tube. The tube was exposed to rays from a 1 KW xenon lamp for 4 hours to effect ultraviolet polymerization on the surface of the gate region of FET and to form a vinyl chloride/vinylidene chloride copolymer membrane. The coated FET was taken out from the quartz tube and aging was carried out overnight at 80° C.

The pH sensitivity of the so prepared electrode was examined according to the method described in Example 2. As a result, it was found that the change of the source potential according to the pH change was as low as 2 mV/pH. Thus, it has been confirmed that the so prepared hydrophobic membrane-coated electrode can be used as a reference electrode. Further, it was observed that even after 24 hours' dipping in water, this electrode was stable.

Obviously, numerous additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A system for measuring chemical properties of substances in an electrolyte solution, comprising:
    a measuring unit comprising an insulated gate FET which selectively detects specific chemical substances;
    a reference electrode comprising an insulated gate FET whose gate region is overlayed with a membrane, said membrane consisting of a hydrophobic organic polymeric membrane material that is impermeable to the electrolyte solution, free of an ionic dissociate group and insensitive to chemical properties of the solution;
    a pseudo reference electrode formed of a good electrical conductor which applies bias to each FET transducer and fixes the electric potential of the electrolyte solution.

2. A system as set forth in claim 1 wherein said measuring unit comprises:
    a FET having an insulated gate region overlaid with an orgaic polymeric membrane containing a ligand capable of selectively absorbing a specific chemical substance so that the sensor is sensitive to said specific chemical substance.

3. A system as set forth in claim 1 wherein said measuring unit comprises:
    a FET having a gate insulating layer arranged in direct contact with the electrolyte solution to determine the pH or pNa of said solution.

4. A system as set forth in claim 1 wherein said hydrophobic organic polymeric membrane comprises:
    a membrane in which the degree of water content is lower than 0.5% by weight.

5. A system as set forth in claim 1, further comprising:
    said hydrophobic organic membrane having a thickness ranging from 500 Å to 10,000 Å.

6. A system as set forth in claim 1 wherein said hydrophobic organic polymeric membrane comprises:
    a membrane of a polymer obtained by polymerizing a monomer selected from the group consisting of mono-olefins, halogenated ethylenes, conjugated dienes and halogenated conjugated dienes.

7. A system as set forth in claim 1 wherein said hydrophobic organic polymeric membrane comprises:
    a membrane of a homopolymer obtained by polymerizing one monomer selected from the group consisting of mono-olefins, halogenated ethylenes, conjugated dienes and halogenated conjugated dienes.

8. A system as set forth in claim 1 wherein said hydrophobic organic polymeric membrane comprises:
    a membrane of copolymer obtained by polymerizing at least two members selected from the group consisting of mono-olefins, halogenated ethylenes, conjugated dienes and halogenated conjugated dienes.

9. A system as set forth in claim 8, further comprising:
    said mono-olefin having 2 to 5 carbon atoms.

10. A system as set forth in claim 8, wherein the mono-olefin is ethylene.

11. A system as set forth in claim 8, wherein said halogenated ethylene comprises:
    a compound represented by the following general formula:

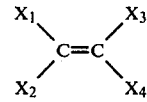

wherein $X_1$, $X_2$, $X_3$ and $X_4$ stand for an atom selected from the group consisting of hydrogen, chlorine and fluorine atoms with the proviso that the case where all of $X_1$ to $X_4$ stands for a hydrogen atom excluded.

12. A system as set forth in claim 8 wherein the halogenated ethylene is trifluoroethylene or tetrafluoroethylene.

13. A system as set forth in claim 8 wherein the halogenated ethylene is vinyl chloride or vinylidene chloride.

14. A system as set forth in claim 8 wherein the conjugated diene or halogenated conjugated diene is a compound represented by the following general formula:

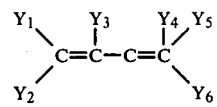

wherein $Y_1$ to $Y_6$ stand for a member selected from the group consisting of hydrogen, chlorine and fluorine atoms and alkyl groups having 1 to 3 carbon atoms.

15. A measuring system as set forth in claim 14, wherein the conjugated diene or halogenated conjugated diene is butadiene or hexachlorobutadiene.

16. A system as set forth in claim 1, wherein said hydrophobic organic polymeric membrane comprises:
    a membrane of a polysiloxane represented by the following general formula:

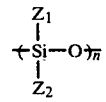

wherein $Z_1$ and $Z_2$ stand for an alkyl or aryl group having 1 to 10 carbon atoms, in which one or more of the carbon atoms may have a halogen or cyano substituent, and n is a number of at least 100.

17. A system as set forth in claim 16, wherein the polysiloxane is polydimethylsiloxane or polyphenylsiloxane.

18. A system as set forth in claim 1, further comprising:
    said measuring unit, said reference electrode and said pseudo reference electrode being formed on a common silicon wafer.

* * * * *